(12) United States Patent
Machiya et al.

(10) Patent No.: US 8,372,071 B2
(45) Date of Patent: *Feb. 12, 2013

(54) HIGH-FREQUENCY TREATMENT TOOL

(75) Inventors: Mamoru Machiya, Saitama (JP); Masayuki Oyatsu, Saitama (JP); Haruo Akiba, Saitama (JP); Shozo Iyama, Saitama (JP); Atsushi Kanaki, Saitama (JP); Hidefumi Akahane, Saitama (JP)

(73) Assignee: FUJINON Corporation, Saitama-shi (JP)

( * ) Notice: Subject to any disclaimer, the term of this patent is extended or adjusted under 35 U.S.C. 154(b) by 1243 days.

This patent is subject to a terminal disclaimer.

(21) Appl. No.: 11/501,789

(22) Filed: Aug. 10, 2006

(65) Prior Publication Data

US 2007/0038213 A1  Feb. 15, 2007

(30) Foreign Application Priority Data

Aug. 12, 2005 (JP) ................................ P2005-234068
Sep. 5, 2005 (JP) ................................ P2005-255869

(51) Int. Cl.
*A61B 18/14* (2006.01)
(52) U.S. Cl. .......................................... 606/47; 606/41
(58) Field of Classification Search .................. 606/41, 606/45–46
See application file for complete search history.

(56) References Cited

U.S. PATENT DOCUMENTS 4,708,137 A  11/1987  Tsukagoshi
2004/0210284 A1*  10/2004  Okada ............................. 607/96
2006/0270969 A1*  11/2006  Toyonaga et al. ............... 604/21
2006/0271079 A1*  11/2006  Akiba et al. .................. 606/167

FOREIGN PATENT DOCUMENTS

| CN | 1605324 A | | 4/2005 |
|---|---|---|---|
| JP | 33-4082 A | | 3/1958 |
| JP | 53-100787 U | | 8/1978 |
| JP | 62-50610 U | | 3/1987 |
| JP | 2004-313537 A | | 11/2004 |
| JP | 2005-521465 A | | 7/2005 |
| JP | 2005-521485 A | | 7/2005 |
| WO | WO 00/28908 | * | 5/2000 |
| WO | WO-00/28908 A1 | | 5/2000 |

* cited by examiner

*Primary Examiner* — Michael Peffley
*Assistant Examiner* — Samantha Good
(74) *Attorney, Agent, or Firm* — Birch, Stewart, Kolasch & Birch, LLP

(57) ABSTRACT

A high-frequency treatment tool comprising: a flexible sheath to be inserted into a treatment tool insertion channel of an endoscope; a treatment tool body provided inside the flexible sheath and comprising: a flexible cord; and a high-frequency knife to which a high-frequency current is applied, formed to the front end of the flexible cord; and a hard cylinder having an electrical insulating property, inserted and fixed inside the flexible sheath, wherein the high-frequency knife comprises blade portions radially provided in its axial direction, each of the blade portions including an engaging part, and wherein, when the high-frequency knife is made to stick out from the hard cylinder, engaging parts of the blade portions abut against a rear end portion of the hard cylinder so that: the high-frequency knife is engaged with the hard cylinder; and communicating channels that communicate an inside and an outside of the flexible sheath are formed between the blade portions adjacent to each other.

7 Claims, 14 Drawing Sheets

HIGH-FREQUENCY TREATMENT TOOL

BACKGROUND OF THE INVENTION

1. Field of the Invention

The present invention relates to a high-frequency treatment tool that is inserted into a treatment tool insertion channel of an endoscope and used for performing a treatment such as incision of a diseased mucous membrane.

2. Description of the Related Art

When a diseased portion such as a tumor is found on the mucous membrane on a body cavity inner wall of the gullet, stomach, duodenum, or colon by endoscopic inspection, a treatment is performed to excise the portion of the diseased mucous membrane by using a high-frequency treatment tool. In this case, to secure safety of the treatment, the treatment is performed under observation through an endoscope, and the high-frequency treatment tool used for the treatment is inserted into the treatment tool insertion channel of the endoscope and guided to the portion to be treated. Herein, on the body cavity inner wall, the submucosal layer exists below the mucosal layer, and the muscle layer is covered by the submucosal layer. The treatment to incise and remove the diseased mucosal layer by using the high-frequency treatment tool must be performed so as not to leave the diseased portion and so as not to damage the muscle layer at all.

The high-frequency treatment tool to be used for incising the mucosal layer is formed by attaching a high-frequency knife formed of an electrode member having a rod-like portion inside a flexible sheath, and to the base end of the flexible sheath, an operating section is joined, and by a remote operation on this operating section, the high-frequency knife can be controlled to stick out and withdraw into the front end of the flexible sheath. By supplying a current to the high-frequency knife sticking out from the flexible sheath, the mucous membrane can be cauterized and incised.

As a structure of the electrode member forming the high-frequency knife, there are available a needle-like knife formed by extending a rod-like electrode member straight, and a hook knife having a hook portion formed by continuously providing a large diameter electrode portion on the front end of the rod-like electrode member or bending the front end of the electrode member into almost an L shape. The needle-like knife is operated so as to stab the mucous membrane, and can incise the mucous membrane by horizontally moving or swinging the electrode member. On the other hand, the hook knife catches the tissue of the mucous membrane by the hook portion on the front end and is operated so as to be drawn to the inserting portion side of the endoscope to incise the mucous membrane.

As described above, during current supply to the high-frequency knife, the high-frequency knife must be reliably maintained in a state without contact with the muscle layer. When the needle-like knife is used, the needle-like knife is positioned ahead of the flexible sheath and punctures the mucous membrane, so that in some cases of performing the treatment, the front end of the needle-like knife cannot be captured in the observation field of the endoscope. Therefore, unless the sticking-out length and sticking-out direction of the needle-like knife from the flexible sheath are accurately controlled, the safety of the treatment cannot be secured.

On the other hand, the hook knife is caught on the mucous membrane under observation through the endoscope, and next, the hook knife is drawn into the treatment tool insertion channel while supplied with a high-frequency current, whereby incising the mucous membrane. Therefore, during operations of the hook knife, the front end of the hook knife can always be operated under observation through the endoscope, so that it can be operated so as not to come into contact with the muscle layer when it is supplied with a current.

However, when using the hook knife, to smoothly catch the tissue of the mucous membrane, the front end of the hook knife must be stable. Therefore, a high-frequency treatment tool having a mechanism for stabilizing the hook knife during actuation is proposed in JP-A-2004-313537. In the high-frequency treatment tool of this JP-A-2004-313537, an electrical insulating member is attached to the front end of the flexible sheath, a through hole is formed in this electrical insulating member, the rod-like portion of the electrode member forming the hook knife is inserted into the through hole, and the hook portion on the front end can come into contact with and separate from the front end outer surface of the electrical insulating member. When it is supplied with current, the electrode member is made to stick out by a predetermined length from the flexible sheath, and the diameter difference between the hole diameter of the through hole and the outer diameter of the electrode member is minimized and the sticking-out length of the electrode member is restricted, whereby stably retaining the electrode member.

During the treatment to excise the diseased portion by using the above-described electrode member, bleeding occurs in some cases, and this may make it impossible to confirm the diseased portion. Therefore, in the electrical insulating member, an opening separate from the through hole for inserting the electrode member is formed, or the through hole is formed into a cross shape or a triangular shape, whereby forming a liquid flow-out portion into which the rod-like portion of the electrode member cannot enter, namely, that is not blocked by the electrode member. A syringe is connected to the base end of the flexible sheath and filled with normal saline solution, and by operating this syringe, the normal saline solution can be jetted to the bleeding portion from the liquid flow-out portion to wash the portion.

In the method according to JP-A-2004-313537, the operations for catching mucous membrane or submucosal layer by the hook knife forming the electrode member, drawing it into the treatment tool insertion channel, and then supplying the hook knife with a current to cauterize and cut the tissue, and leading-out the hook knife again from the treatment tool insertion channel, are repeated, so that the operations become complicated and difficult, and operation efficiency cannot be obtained. Therefore, it takes a long time to perform the treatment to remove the diseased mucous membrane, and accordingly, the pain of the examinee and the burden on the operator may increase. The hook portion is always exposed to the outside, and for example, during insertion into the treatment tool insertion channel, if the electrode member is supplied with a current by mistake, it may damage the channel inner wall.

In addition, in the electrical insulating member provided on the front end of the flexible sheath, to form the fluid flow-out portion that the electrode member cannot enter, a plurality of through holes are formed or a through hole with a complicated shape is formed. Herein, the electrical insulating member must be made of a material with excellent heat resistance, and therefore, desirably, it is made of ceramic, however, it is difficult to form the through hole having the above-described shape in this ceramic.

SUMMARY OF THE INVENTION

The invention was developed in view of these circumstances, and an object thereof is to realize safe and efficient treatment by using a high-frequency treatment tool that uses a needle-like knife and is simple in structure.

To achieve the above-described object, according to the invention, there is provided a high-frequency treatment tool comprising: a flexible sheath that can be inserted into a treatment tool insertion channel of an endoscope; a treatment tool body that is provided inside the flexible sheath, the treatment tool body comprising a flexible cord and a high-frequency knife to which a high-frequency current is applied, the high-frequency knife being formed to the front end of the flexible cord; and a hard cylinder having an electrical insulating property, the hard cylinder being inserted and fixed inside the flexible sheath so that a front end face of the hard cylinder forms almost the same plane as a front-end face of the flexible sheath, wherein the high-frequency knife comprises a plurality of blade portions radially provided at predetermined positions in an axial direction of the high-frequency knife, each of the blade portions including an engaging part, and wherein, when the high-frequency knife is made to stick out from the hard cylinder, engaging parts of the blade portions abut against a rear end portion of the hard cylinder so that: the high-frequency knife is engaged with the hard cylinder; and communicating channels that communicate an inside and an outside of the flexible sheath are formed between the blade portions adjacent to each other.

In the first embodiment of the invention, the hard cylinder has a hole diameter larger than an outer diameter of the high-frequency knife, the rear end portion of the hard cylinder is formed into a tapered surface inclined inward from its outer circumferential side to its inner circumferential edge, front end faces of the blade portions are formed into inclined portions serving as the engaging parts, the inclined portions corresponding to the tapered surface of the hard cylinder, and when the high-frequency knife is made to stick out from the hard cylinder, the inclined portions of the blade portions abut against the tapered surface of the hard cylinder so that the high-frequency knife is engaged with the hard cylinder.

The hard cylinder fixedly provided in the flexible sheath is a cylindrical member having a through hole with a hole diameter that allows the high-frequency knife to be inserted inside, and the rear end thereof is formed into a tapered surface, so that its shape is very simple. Herein, the tapered surface forming the rear end face of the hard cylinder serves as a draw-in tapered surface for drawing the high-frequency knife into the through hole. Therefore, the tapered surface can be formed from the outer circumferential edge of the hard cylinder, or can be formed from the middle portion. However, the distance from the outer circumferential edge to the tapered surface is set shorter than the radius of the front end of the high-frequency knife, and the tapered surface must be extended to the inner circumferential edge.

On the high-frequency knife, stopper projections serving as the blade portions are formed at positions at a predetermined distance from the front end of the high-frequency knife. The number of stopper projections is at least two, and preferably, three stopper projections are provided at intervals of 120 degrees or four stopper projections are provided at intervals of 90 degrees. The stopper projections come into contact with and separate from the tapered surface of the hard cylinder, and when the high-frequency knife is made to stick out from the flexible sheath, the surfaces of the stopper projections come into contact with the tapered surface to perform the function as stoppers to restrict the sticking-out length from the front-end face of the flexible sheath, and perform the function to reliably guide the high-frequency knife toward the position of the central axis line of the flexible sheath and stably retain the high-frequency knife on the central axis line.

In the maximum sticking-out state in that the stopper projections are in contact with the base end of the hard cylinder, in the inner diameter portion of the hard cylinder, between the stopper projections adjacent to each other, communicating channels for feeding a liquid to the portion being treated and suctioning the liquid are formed. It is desirable that the angle of inclination of the front end faces of the stopper projections and the tapering angle of the hard cylinder almost match with each other, however, a slight difference between the angles is allowed as long as this deteriorates the above-described functions.

As described above, the hard cylinder comprises an electrical insulating member, however, heat resistance is also required. Therefore, the hard cylinder can also be made of a synthetic resin, however, this is a member with a simple cylindrical shape, so that workability is not necessarily set as a material requirement. Therefore, the hard cylinder can be made of ceramic that is difficult to be processed. On the other hand, the stopper projections are made of a hard material, and are not necessarily made of an electrical insulating material. Therefore, it can be made of, for example, a metal material that is easily processed.

By forming the front-end face of the flexible sheath and the front end face of the hard cylinder into the same plane, an annular end wall that comes into contact with the body cavity inner wall is formed. When the treatment tool body is made to contact the body cavity inner wall, to minimize the contact surface pressure, the annular end wall must have a wide area. In this point of view, the hole diameter of the hard cylinder is desirably set as small as possible. Between the inner surface of the hard cylinder and the outer surface of the high-frequency knife, at portions between the stopper projections adjacent to each other, communicating channels are formed, and the path areas of the communicating channels are desirably formed as large as possible. For this, setting the inner diameter of the hard cylinder as large as possible is more advantageous. To satisfy the above-described contradictory requirements, in the circle of the outer diameter of the flexible sheath, the annular end wall occupies 65 through 90% of the entire area, and more preferably, occupies 80%.

In the second embodiment of the invention, the high-frequency knife further comprises a rod-like electrode that can be inserted through the hard cylinder in a loosely fitted manner, said plurality of blade portions being provided on a base-end side of the rod-like electrode, each of the blade portions has: an outer surface having a size to almost contact with an inner circumferential surface of the hard cylinder; and a stopper surface, serving as the engaging part, formed at a base-end portion of the blade portion, the stopper surface protruding further to an outer circumferential side than a hole diameter of the hard cylinder, and when the high-frequency knife is made to stick out from the hard cylinder, stopper surfaces of the blade portion abut against an end face of the hard cylinder so that the high-frequency knife is engaged with the hard cylinder.

As in the above, the hard cylinder has an extremely simple cylindrical shape, and the hard cylinder can be easily formed of, for example, a ceramic material. However, it is not always necessary to form the hard cylinder of a ceramic material, and it may be formed of a synthetic resin or the like excellent in heat resistance. On the other hand, the high-frequency knife is formed of a conductive member, for which the rod-like electrode and the blade portions and stopper surfaces are integrally formed of a metal material that is easy to process.

By operating the flexible cord by pushing and pulling in the flexible sheath, this can be displaced into a condition where the high-frequency knife is stored inside the flexible sheath and a condition where the same is protruded from the front end of the flexible sheath. When the high-frequency knife has protruded by a predetermined amount, since the stopper surfaces abut against the base-end face of the hard cylinder, this position equals the maximum protruding position of the high-frequency knife, and a treatment such as incision is executed in this condition. Accordingly, the protrusion length of the rod-like electrode of the high-frequency knife at the maximum protruding position is set so as to be optimal according to a treating site. For example, when a mucosal stripping treatment is conducted, the protrusion length of the rod-like electrode is longer than the thickness dimension of the mucosa and is shorter than the total thickness dimension of the mucosa and submucosal layer. Thereby, safety is secured when the treatment is conducted and it can be prevented from leaving the diseased mucosa unremoved.

For the high-frequency knife, a plurality of blade portions are provided on the base-end side of the rod-like electrode, and since the outer surfaces of these blade portions virtually contact with the inner surface of the hard cylinder, the high-frequency knife is aligned with respect to the flexible sheath and is stably held with out producing a shake or the like. Therefore, in this regard, it is desirable to increase the number of the blade portions and expand the width dimension as wide as possible. However, the intervals between the mutually adjacent blade portions serve as communicating channels that communicate with the inside of the flexible sheath with the outside thereof, and a fluid such as a physiological saline solution is supplied from these communicating channels and is suctioned from the body. In order to expand the channel area of the communicating channels, it is necessary to reduce the number of the blade portions and narrow the width thereof conversely. Although the blade portions are provided a minimum of two points, these are provided preferably at three points with intervals of 120° or at four points with intervals of 90°. In addition, it is desirable to provide the width dimension of the blade portions as a minimum width where stability thereof is not lost based on an external force that acts on the high-frequency knife when conducting a treatment such as incision. In view of stability of the high-frequency knife, it is desirable to make the outer surfaces of the respective blade portions almost slidingly contact with the inner circumferential wall of the through-hole of the hard cylinder. However, in order to make the high-frequency knife be easily inserted and removed with respect to the hard cylinder, a slight gap may be produced therebetween.

When the high-frequency knife has been drawn into the flexible sheath, this is sometimes positioned further at the base-end side than the hard cylinder. In this case, in order to lead the front end of the rod-like electrode smoothly and reliably to the through-hole of the hard cylinder, it is sufficient to mount a lead-in member at a position on the base-end side of the hard cylinder. The lead-in member is a ring-like member, whose end face on the base-end side is inclined toward the front-end side. The lead-in member has an inside diameter that allows inserting the high-frequency knife there through. Since the lead-in member is not exposed outside, it is not always necessary to form the same of an electrical insulating member, and it can be easily formed of a plastic material, a metal material, or the like.

The front end face of the flexible sheath is a plane almost identical to the front end face of the hard cylinder, whereby an annular end wall to be an abutting surface against the inner wall of a body cavity is formed. And, in order to have as small a surface pressure as possible when the treatment tool body is abutted against the inner wall of a body cavity, it is necessary that the end wall secures a wide area, and in this regard, it is desirable to reduce the hole diameter of the hard cylinder as much as possible. On the other hand, in the through hole of the hard cylinder, communicating channels are formed at parts between the mutually adjacent blade portions, it is desirable that the channel area of the communicating channels is great. Therefore, in view of these circumstances, the inside diameter of the hard cylinder is appropriately set.

By employing the above structure, effects are provided such that it becomes possible, by mounting a hard cylinder with a simple structure in a flexible sheath, to regulate the protrusion amount of a high-frequency knife formed of a rod-like electrode, and when a treatment such as incision is carried out, to secure safety of the high-frequency knife so as to enable a safe and swift treatment, and to supply and discharge a fluid during the treatment.

DETAILED DESCRIPTION OF THE INVENTION

Hereinafter, an embodiment of the invention will be explained based on the drawings. First, an entire construction of the high-frequency treatment tool is shown in FIG. 1, a main part enlarged section of the first embodiment of the high-frequency treatment tool is shown in FIG. 2, and a main part enlarged section of the second embodiment of the high-frequency treatment tool is shown in FIG. 8.

Figure 1:
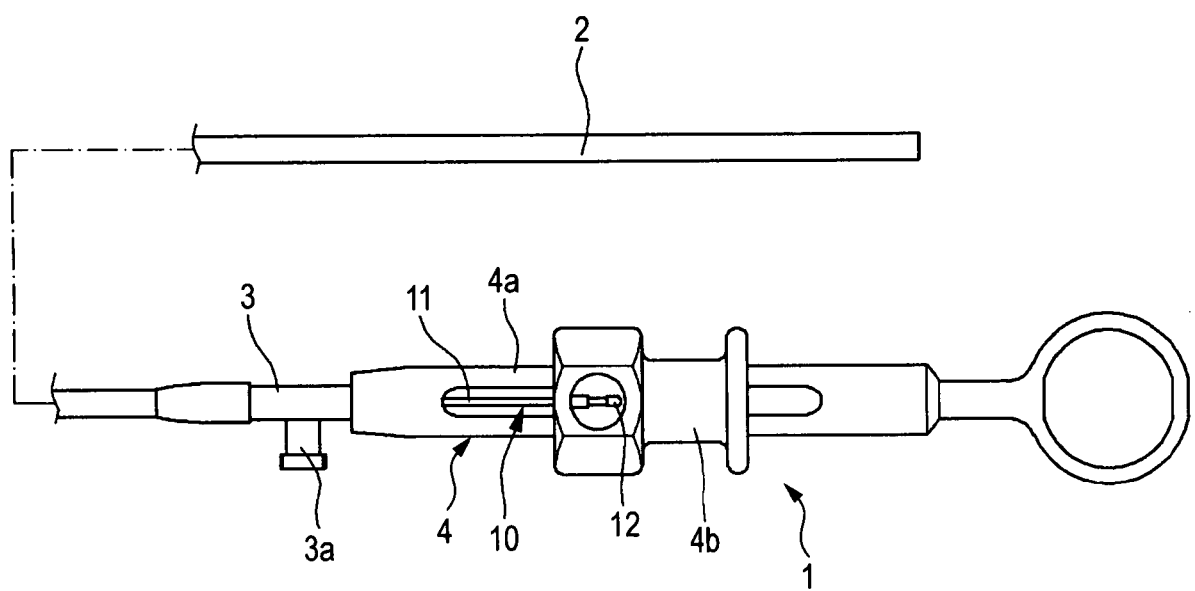
FIG. 1 is an entire construction view of a high-frequency treatment tool of an embodiment of the invention.
Figure 2:
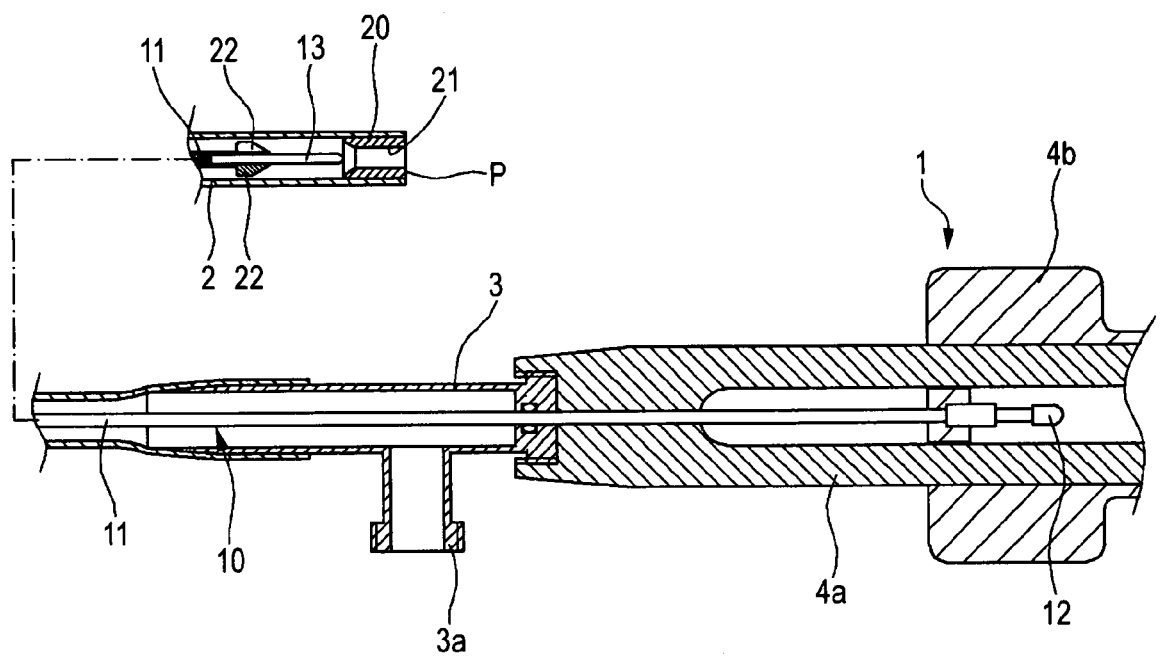
FIG. 2 is a main part enlarged view of FIG. 1.
Figure 8:
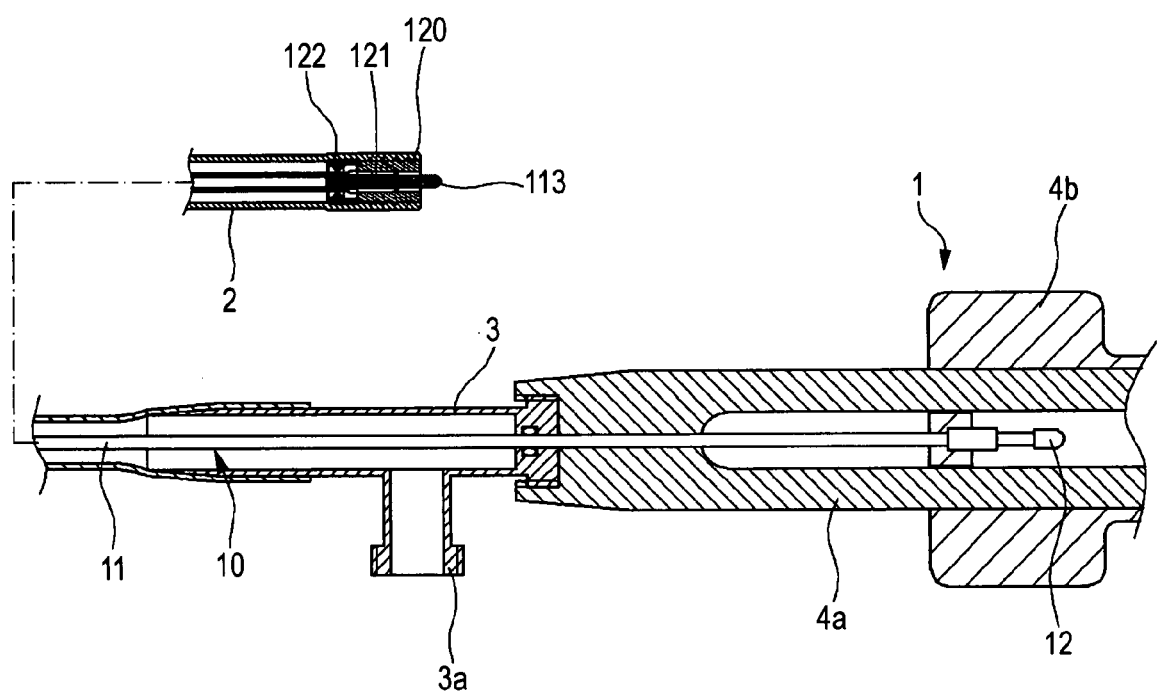
FIG. 8 is a main-part enlarged cross-sectional view of FIG. 1.

First, in FIG. 1, FIG. 2 and FIG. 8, the reference numeral 1 denotes a high-frequency treatment tool, and this high-frequency treatment tool 1 has a long flexible sheath 2, and to the base end of this flexible sheath 2, a connecting pipe 3 is joined, and to the other end of this connecting pipe 3, an operating section 4 is joined. The operating section 4 includes a main body shaft 4a joined to the connecting pipe 3 and a slider 4b that is fitted to the main body shaft 4a and is slidable in the axial direction of the main body shaft 4a. To the slider 4b, the base end of a flexible cord 11 forming the treatment tool body 10 is joined.

First Embodiment

Figure 3:
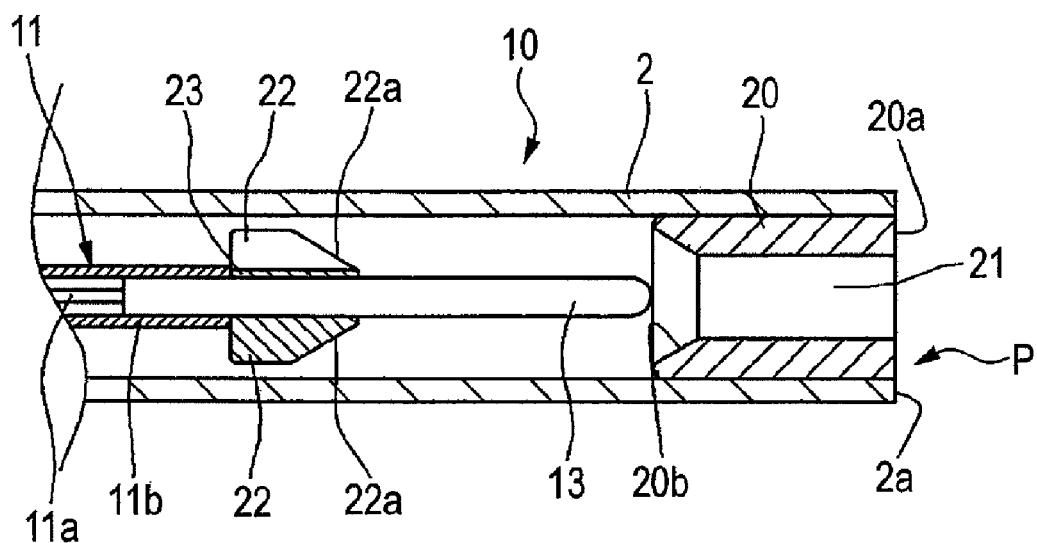
FIG. 3 is an enlarged sectional view of the front end portion of the treatment tool body.
Figure 4:
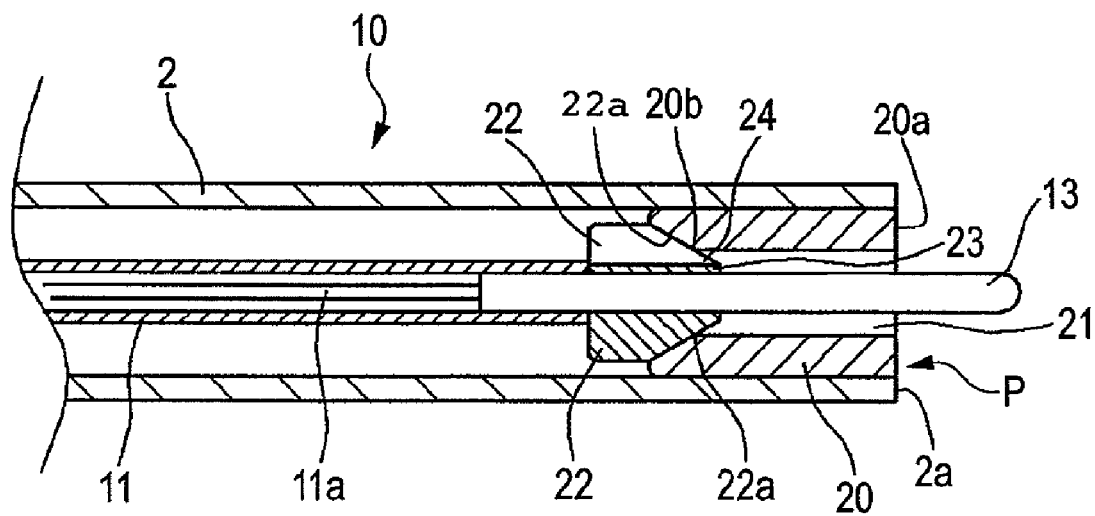
FIG. 4 is a sectional view similar to FIG. 3, showing the electrode member made to stick out.

Hereinafter, the first embodiment of the invention will be explained. FIG. 3 and FIG. 4 show the section of the front end portion of the high-frequency treatment tool in actuating states different from each other. As clearly seen in FIG. 3, the flexible cord 11 is formed by inserting, for example, the outer circumference of a lead wire 11a into an insulating coating 11b, and has flexibility in at least the bending direction. The base end of the lead wire 11a of the flexible cord 11 sticks out by a predetermined length from the portion joined to the slider 4b to form a contact portion 12. This contact portion 12 is connected to an unillustrated high-frequency power supply apparatus in a disconnectable manner.

The flexible cord 11 forming the treatment tool body 10 is extended to the inside of the flexible sheath 2 through the inside of the connecting pipe 3 from the portion attached to the slider 4b. The needle-like knife 13 is provided so as to stick out from and withdraw into the front end of the flexible sheath 2. The needle-like knife 13 is preferably formed of a hard needle-like or rod-like conductive member having a spherical front end and a predetermined length, that is, has no hook portion, and is electrically connected to the lead wire 11a of the flexible cord 11, and the predetermined length thereof is exposed to the outside, and when it is supplied with a current, this portion acts on the internal body tissue and cauterizes and incises this tissue.

The reference numeral 20 denotes a hard cylinder, and this hard cylinder 20 is formed of a hard member inserted into and fixed to the front end of the flexible sheath 2, and is made of a material having an electrical insulating property and a heat resistance, preferably, ceramic. On the outer surface of the hard cylinder 20, a three-stepped surface whose steps are different in diameter from each other although these are slight is formed, and the front end side is the smallest in diameter and the rear end is the largest in diameter. Between the outer surface of this hard cylinder 20 and the inner surface of the flexible sheath 2, an adhesive is interposed, and due to this adhesive and the steps on the outer surface, the hard cylinder 20 is fixed to the front end side of the flexible sheath 2 so as not to come off.

In the hard cylinder 20, a through hole 21 is formed, and the front end face 20a thereof is a surface orthogonal to the axis line, and the front end face 20a forms almost the same plane as the front end face 2a of the flexible sheath 2, and by these end faces 2a and 20a, an annular end wall P is formed. The hole diameter of the through hole 21 of the hard cylinder 20 is set larger than the outer diameter of the needle-like knife 13, and therefore, the needle-like knife 13 is inserted into this insertion hole 21 in a freely fitting state.

The needle-like knife 13 can be displaced between in a state in that it is drawn closer to the base end side than the hard cylinder 20 as shown in FIG. 3 and in a state in that it sticks out by a predetermined length from the annular end wall P. To make it reliable to draw the front end of the needle-like knife 13 to the inside of the hard cylinder 20, the rear end face 20b of the hard cylinder 20 is tapered. The tapered surface of the rear end face 20b is inclined at a predetermined angle inwardly toward the inner circumferential edge from the outer circumferential side, and a predetermined width of the outer circumferential edge is formed into a round shape. The width of this round portion is set equal to or less than the radius of the needle-like knife. Therefore, when the needle-like knife 13 is operated so as to be pushed out from the front end of the flexible sheath 2, the front end of this needle-like knife 13 is guided so as to get onto the tapered surface of the rear end face 20b of the hard cylinder 20 and is oriented in the central axis direction of this hard cylinder 20.

Figure 5:
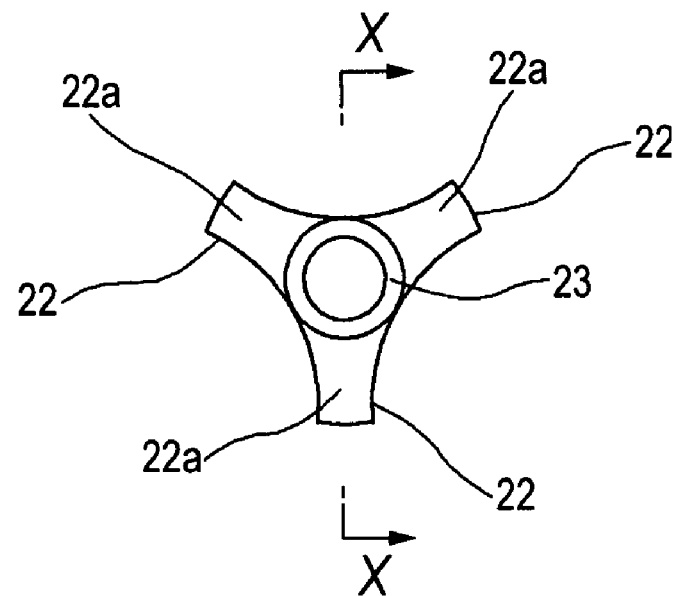
FIG. 5 is a front view of a stopper wall.
Figure 6:
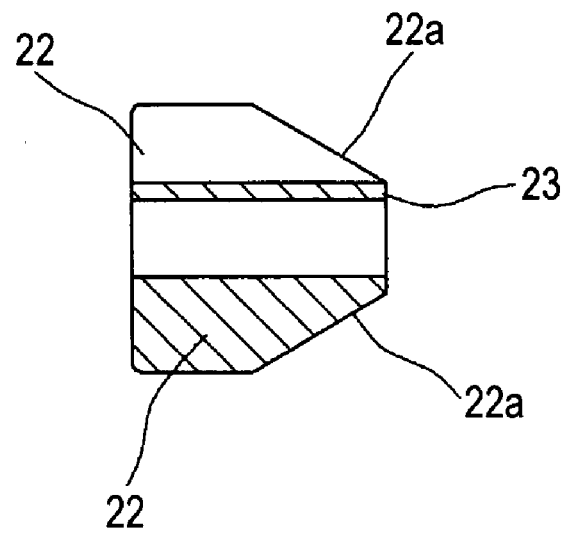
FIG. 6 is a sectional view on X-X of FIG. 5.

The needle-like knife 13 is provided with stopper projections (blade portions) 22 at positions a predetermined distance closer to the base end side from the front end. The stopper projections 22 are radially projectedly provided at three points at phases of 120 degrees from each other on the outer circumference of the needle-like knife 13 as shown in FIG. 5 and FIG. 6, and the projection heights are lower than the inner circumferential surface of the flexible sheath 2 and higher than at least the inner circumferential edge of the through hole 21 formed in the hard cylinder 20. Each stopper projection 22 has a predetermined thickness, and the front end face 22a thereof is formed into an inclined surface projecting toward the front end side of the high-frequency treatment tool 1. The angle of inclination of the front end face 22a of the stopper projection 22 almost corresponds to the angle of inclination of the rear end face 20b of the hard cylinder 20. Herein, the stopper projections 22 are made of a metal member of stainless steel or the like integrally provided on a cylinder 23 fitted to the needle-like knife 13, and the cylinder 23 is fixed to the needle-like knife 13 by means of welding or the like.

Therefore, as clearly seen in FIG. 4, when the needle-like knife 13 is made to stick out by a predetermined length from the front end of the flexible sheath 2, that is, from the annular end wall P, the front end faces 22a of the stopper projections 22 come into entire contact with the rear end face 20b of the hard cylinder 20, and this position is the maximum sticking-out position of the needle-like knife 13. Herein, at the maximum sticking-out position of the needle-like knife 13, the distance from the annular end wall P to the front end of the needle-like knife 13 is set larger than the thickness of the mucous membrane in the body cavity inner wall and smaller than the total thickness of the mucous membrane and submucosal layer.

Figure 7:
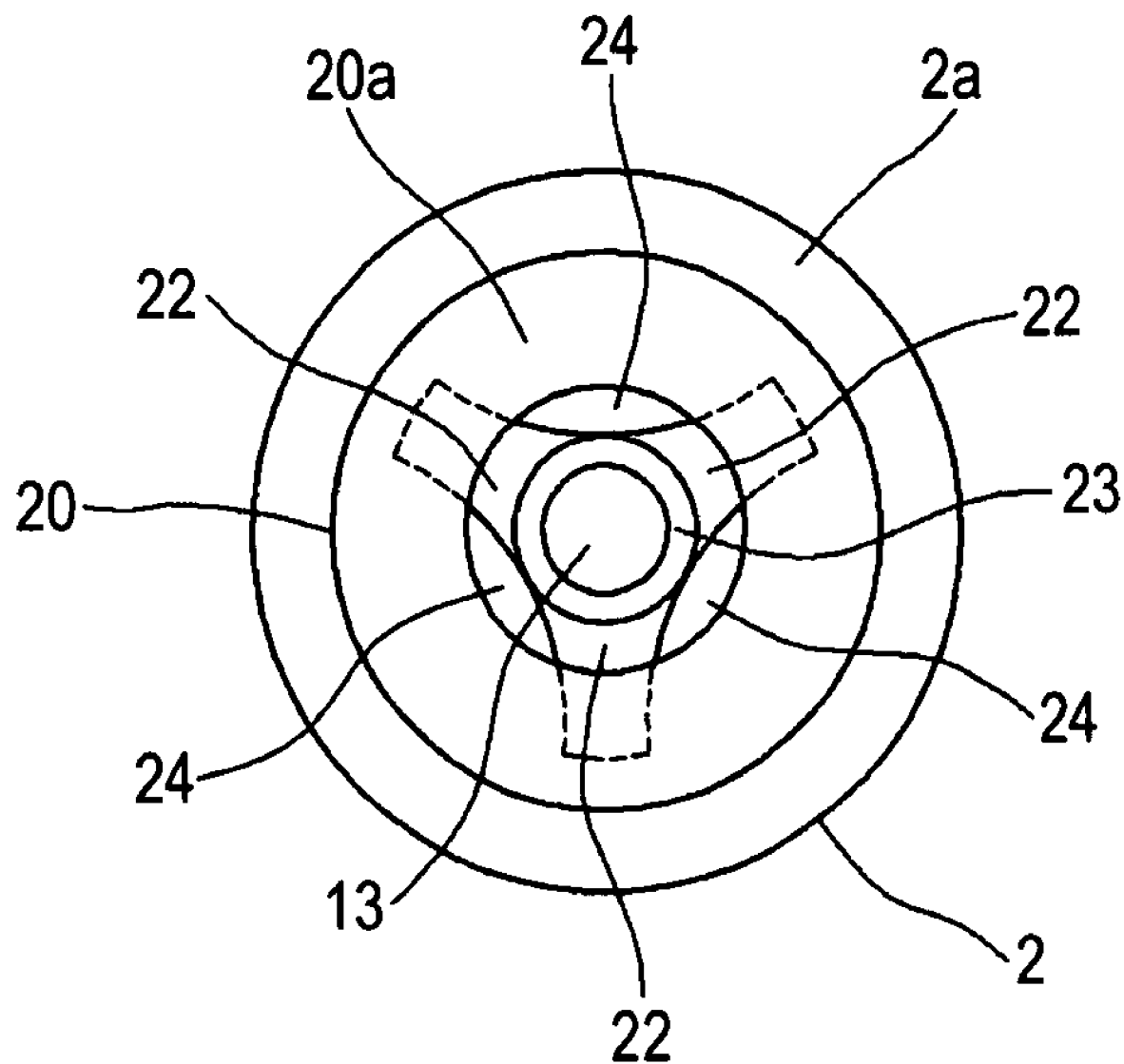
FIG. 7 is a front view of FIG. 4.

When the needle-like knife 13 comes to the maximum sticking-out position, as shown in FIG. 7, based on the diameter difference between the outer circumference of the needle-like knife 13 and the hole diameter of the through hole 21 of the hard cylinder 20, three communicating channels 24 are formed between stopper projections 22 adjacent to each other. The connecting pipe 3 provided on the base end side of the high-frequency treatment tool 1 has a connection port 3a, and to this connection port 3a, a syringe for supplying a liquid such as normal saline solution and a suction pipe, etc., are connected.

Second Embodiment

Hereinafter, the second embodiment of the invention will be explained.

Figure 9:
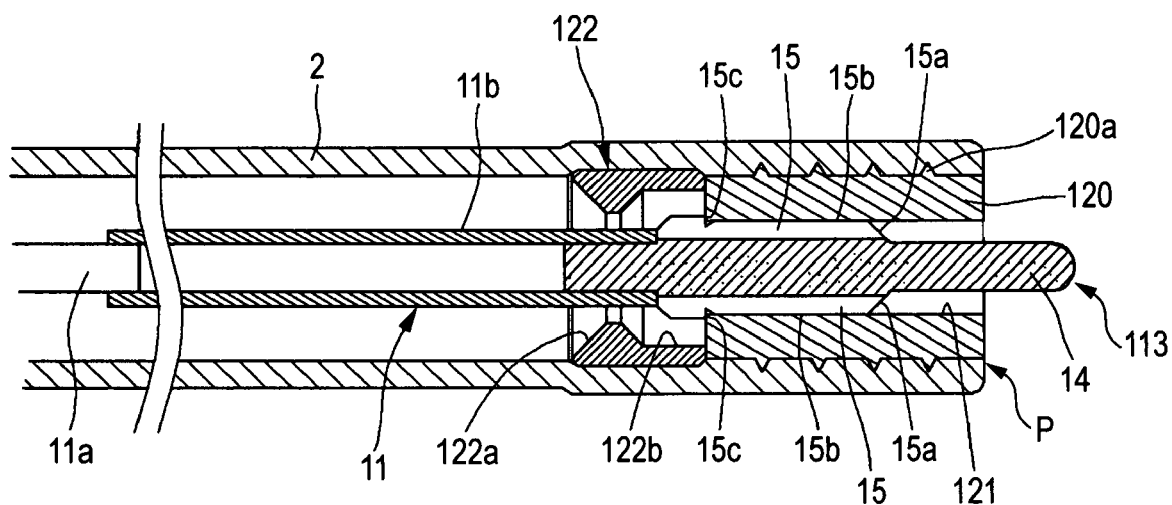
FIG. 9 is an enlarged cross-sectional view of a front-end part of the high-frequency treatment tool.

As shown in FIG. 8, the flexible code 11 includes a conductive line portion 11a formed of a flexible member whose outer circumferential portion has been applied with insulating coating, a base-end portion of the conductive line portion 11a is provided while being protruded by a predetermined length from a coupling portion to the slider 4b, a contact portion 12 is provided on the base-end portion, and the contact portion 12 is attachably and detachably connected to an unillustrated high-frequency power unit. As shown in FIG. 9, the front end of the conductive line portion 11a is coupled with a hollow wire 11b. The hollow wire 11b is formed of a conductive member having flexibility in a bending direction, and an outer circumferential surface thereof is coated with an insulating member. Therefore, the conductive line portion 11a is electrically conductive with the hollow wire 11b, and the outer surface thereof is insulated.

The flexible cord 11 formed of the conductive line portion 11a and hollow wire 11b is extended into the flexible sheath 2 through the inside of the connection pipe 3 from the attaching portion to the slider 4b. In addition, at a front-end portion of the flexible sheath 2, a high-frequency knife 113 is provided so that projection and retraction is possible therefrom. The high-frequency knife 113 is composed of a rod-like electrode 14 that is preferably formed of a hard needle-like or rod-like conductive member having a predetermined length whose front end has a spherical form, namely, without a hook portion and blade portions 15 provided at an outer circumferential portion of the rod-like electrode 14. A base-end portion of the rod-like electrode 14 is inserted into the hollow wire 11b of the flexible cord 11, whereby the high-frequency knife 113 is electrically connected with the contact portion 12 via the hollow wire 11b and conductive line portion 11a. The high-frequency knife 113 is exposed outside from the flexible sheath 2 by a part equal to the predetermined length, and this part acts on a body tissue so as to cauterize the tissue for a treatment such as incision when current is applied.

Figure 10:
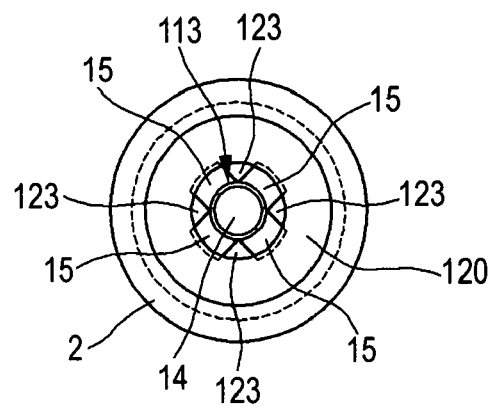
FIG. 10 is a front view of the high-frequency treatment tool.

As shown in FIG. 9 and FIG. 10, a hard cylinder 120 is inserted and fixed to the front-end portion of the flexible sheath 2. The hard cylinder 120 is formed of a member excellent in an electrical insulating property and a heat resistance, preferably, a ceramic material. A spiral protrusion 120a is provided on the outer surface of the hard cylinder 120, so that the hard cylinder 120 is inserted by screwing into the flexible sheath 2. Moreover, an adhesive is interposed between the outer surface of the hard cylinder 120 and inner surface of the flexible sheath 2, and by an effect of the adhesion and the protrusion 120a on the outer surface, the hard cylinder 120 is fixed toward the front-end side of the flexible sheath 2 so as not to fall off.

In the hard cylinder 120, a through-hole 121 to protrude and retract the high-frequency knife 113 therefrom is pierced so as to penetrate in the axis direction. In addition, both end faces of the hard cylinder 120 are faces orthogonal to an axis line thereof. The hard cylinder 120 is inserted up to a position where the front end face becomes a plane almost identical to the front end face of the flexible sheath 2, so that owing to these front end faces of the flexible sheath 2 and hard cylinder 120, the front end face of the flexible sheath 2 has an annular end wall P. The hole diameter of the through-hole 121 of the hard cylinder 120 is greater than the outside diameter of the high-frequency knife 113, so that the rod-like electrode 14 of the high-frequency knife is inserted through the through-hole 121 in a loosely fitted condition.

Figure 11:
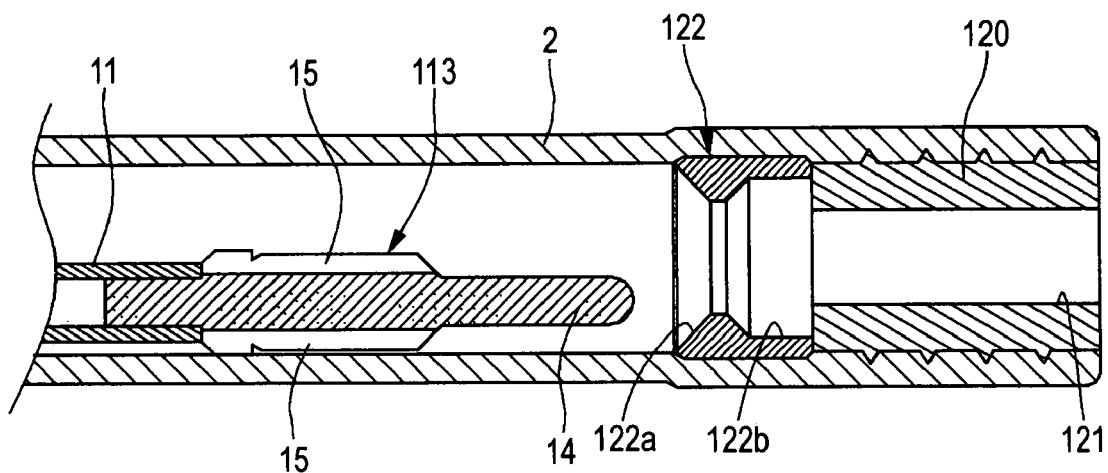
FIG. 11 is a cross-sectional view similar to FIG. 9 showing a condition where a high-frequency knife has been drawn further to a base-end side than a lead-in member.
Figure 12:
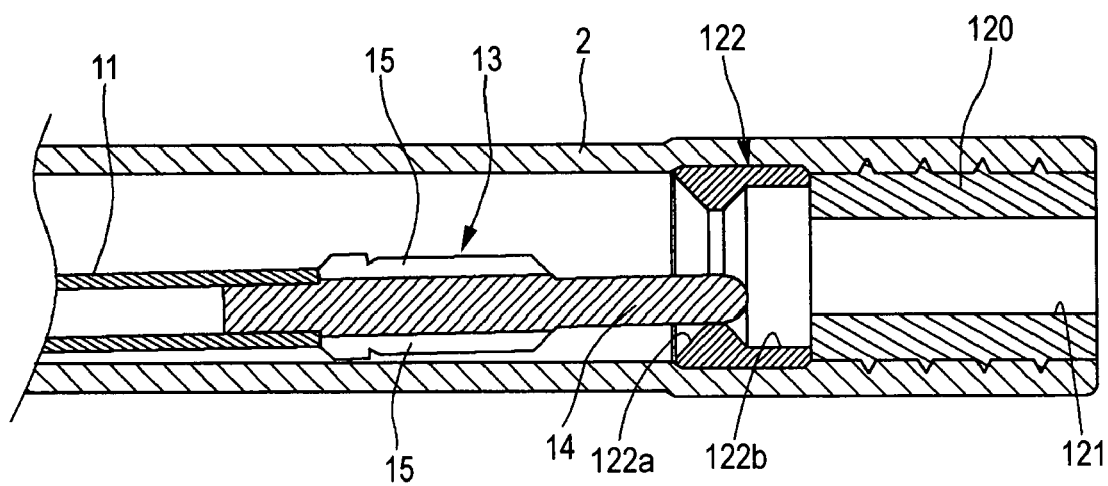
FIG. 12 is a cross-sectional view similar to FIG. 9 showing a condition where a rod-like electrode of the high-frequency knife has been guided to the lead-in member.

On the base-end portion of the hard cylinder 120, a lead-in member 122 to reliably lead the high-frequency knife 113 into the through-hole 121 from a position further at the base-end side than the through-hole 121 is mounted. The lead-in member 122 is a ring-shaped member formed of stainless steel or the like, whose base end face is a tapered surface 122a that inclines toward the front-end side as it goes from the outer circumferential side toward the inner circumferential side, whereby the high-frequency knife 113 is lead into the through-hole 121. Namely, normally, the high-frequency knife 113 has been drawn further to the base-end side than the hard cylinder 120 as shown in FIG. 11, and in this condition as shown in FIG. 12, by being led toward the direction of the through-hole 121 along the tapered surface 122a, the front end of the rod-like electrode 14 is led into the through-hole 121. A part with the minimum diameter in the tapered surface 122a has a size to pass the high-frequency knife 13 therethrough. Moreover, a concave portion 122b is formed at the front-end side from the minimum diameter portion of the lead-in member 122, and an annular end face with a large diameter formed by the concave portion 122b abuts against the base end face of the hard cylinder 120. Therefore, an inside part at the end face of the hard cylinder 120 is exposed. Consequently, a stopper surface 15c formed on the blade portion 15 of the high-frequency knife 113 reliably abuts against the base end face of the hard cylinder 120.

Figure 13:
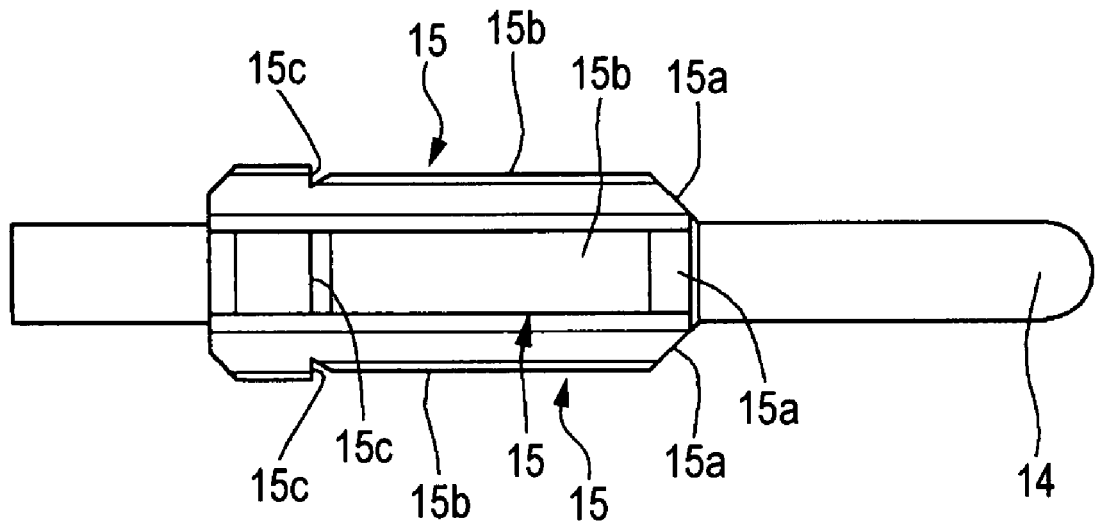
FIG. 13 is a plan view of the high-frequency knife.
Figure 14:
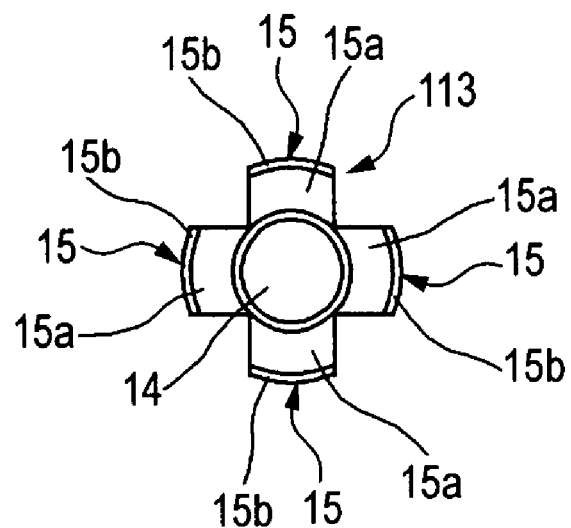
FIG. 14 is a front view of the high-frequency knife.

The rod-like electrode 14 of the high-frequency knife 113 can be applied with a high-frequency current by a power supply from the contact point 12 via the conductive line portion 11a and hollow wire 11b of the flexible cord 11. The rod-like electrode 14 is, as shown in FIG. 13 and FIG. 14, a conductive straight rod-like member having a predetermined length, whose front end has a spherical form. In addition, as the blade portions 15, four blade portions are provided on the base-end side of the rod-like electrode 14 at positions with an angle of 90° from each other, and these blade portions 15 are radially protruded outward. A front end face 15a of the blade portion 15 is an inclined plane to lead the blade portion 15 to the through-hole 121 of the hard cylinder 120, an outer surface 15b of the blade portion 15 forms an arc shape almost coincident with the curvature of the through-hole 121 and has a predetermined length. Therefore, when the high-frequency knife 113 is inserted into the through hole 121 of the hard cylinder 120, the outer surfaces 15b of the blade portions 15 provided at four points virtually sildingly contact with the inner surface of the through-hole 121. Consequently, the high-frequency knife 113 is aligned with respect to the axis line of the hard cylinder 120, and is stably held so as not to shake in vain even when an external force acts on the front-end part of the rod-like electrode 14 thereof.

Furthermore, a step to have a tall height is formed at a part on the base-end side of the blade portion 15, and the stepped wall serves as the stopper surface 15c. When the high-frequency knife 113 is inserted into the through-hole 121 of the hard cylinder 120, the stopper surface 15c can proceed up to a position to abut against the base end face of the hard cylinder 120 and cannot protrude any further. Namely, the stopper surface 15c regulates the maximum protrusion length of the rod-like electrode 14 of the high-frequency knife 113 from the flexible sheath 2. The high-frequency treatment tool 1 is used for a treatment to strip a diseased mucosal part on the inner wall of a body cavity, and the maximum protrusion length from the annular end wall P that forms the front end of the flexible sheath 2 in the rod-like electrode 14 of the high-frequency knife 113 is set so as to be longer than the thickness dimension of a mucosa on the inner wall of a body cavity and shorter than the total thickness of the mucosa and a submucosal layer.

When the high-frequency knife 113 has reached the maximum protruding position, as is apparent from FIG. 10, based on a difference in diameter between the outside diameter and outer circumference of a shaft part of the high-frequency knife 113 and hole diameter of the through-hole 121 of the hard cylinder 120, four roughly fan-shaped communicating channels 123 are formed at parts between the mutually adjacent blade portions 15 and 15. The connection pipe 3 provided at a part of the base-end side of the high-frequency treatment tool 1 has a connection port 3a. The connection port 3a is connected with a syringe that supplies a fluid such as a physiological saline solution, suction piping, or the like. Therefore, by connecting a syringe filled with a physiological saline solution to the connection port 3a in advance and then operating the syringe when the high-frequency knife 113 has protruded as far as it will go from the hard cylinder 120, the physiological saline solution is injected from the circumference of the rod-like electrode 14 via the communicating channels 123. In addition, connection of the suction piping makes suction from the communicating channels 123 possible. Even in a condition where the high-frequency knife 113 is arranged further at the base-end side than the hard cylinder 120, supply and suction of fluid are possible.

Figure 15:
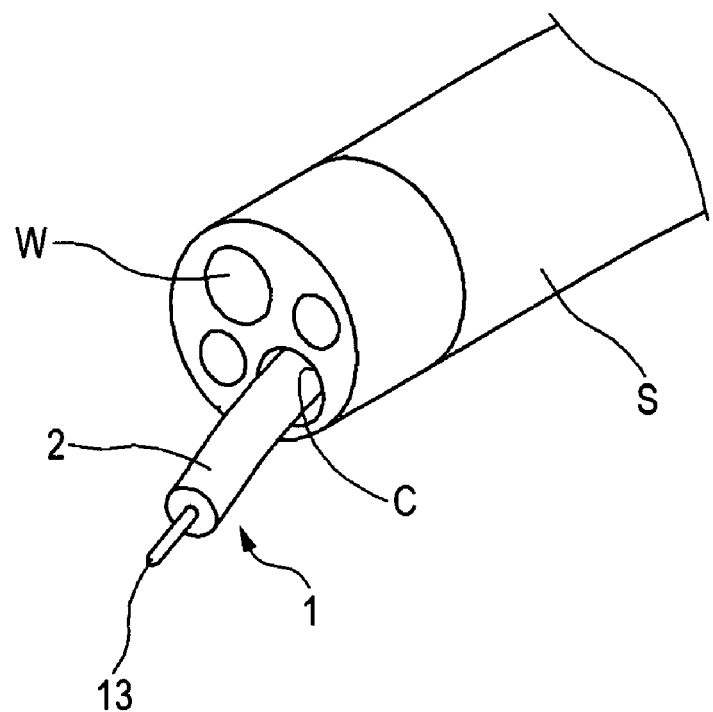
FIG. 15 is an external view showing a state in that the high-frequency treatment tool of an embodiment of the invention is led out from a treatment tool insertion channel of an endoscope.

As shown in FIG. 15, the high-frequency treatment tool 1 constructed as described above is inserted into a body cavity via an treatment tool insertion channel C provided in an endoscope inserting portion S including an observing portion W, and when a diseased mucous membrane exists on the body cavity inner wall of, for example, the gullet, the stomach, the duodenum, or the colon, the high-frequency treatment tool 1 is used for performing a treatment to exfoliate and excise this diseased mucous membrane. One example of a treatment to excise this diseased mucous membrane will be explained. For example, this treatment is performed when a diseased portion is found on the mucous membrane as a result of endoscopic inspection.

Figure 16:
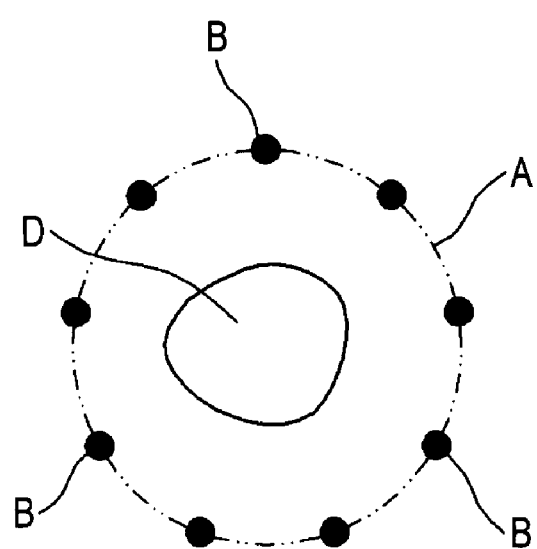
FIG. 16 is a plan view of marking of a diseased mucosal region.

Therefore, first, as shown in FIG. 16, the mucous membrane including the diseased portion D to be excised is marked so that the marking surrounds the diseased mucosal region D. This marking region is set to be a range so that the diseased portion can be completely removed while minimizing damages on the healthy mucous membrane. The marking can be performed by, for example, making cauterizing spots B at necessary portions around the diseased mucosal region D, and to form the cauterizing spots B, the high-frequency treatment tool 1 can be used. Namely, the front end of the endoscope inserting portion S is made to face the outer edge of the diseased mucosal region D at a predetermined distance, and in this state, the high-frequency treatment tool 1 is inserted into the treatment tool insertion channel C and the front end thereof is made to contact the mucous membrane surface. As shown in FIGS. 3 and 11, at this time, the needle-like knife (high-frequency knife) 13 is withdrawn to the position closer to the base end side than the hard cylinder 20. No member sticks out from the annular end wall P of the front end of the high-frequency treatment tool 1, and this annular end wall P comes into entire contact with the mucous membrane surface.

In this condition, the needle-like knife 13 (113) is protruded by operating the operating section 4 of the high-frequency treatment tool 1. At this time, in the second embodiment for example, the front-end portion of the rod-like electrode 14 of the high-frequency knife 113 is guided to the tapered surface 122a of the lead-in member 122 passing through a condition shown in FIG. 6, and is reliably led into the through-hole 121 of the hard cylinder 120. In this condition, when a high-frequency current is applied to the high-frequency knife 113, a site in the mucosa with which the high-frequency knife 113 is in contact is cauterized so that marking is applied. Herein, at the time of this marking, the needle-like knife 13 (113) does not have to penetrate the mucosal layer, and it is only required that the mucous membrane surface is cauterized to a degree that enables recognition of this surface by an image obtained through the observing portion W of the endoscope inserting portions. Namely, when the needle-like knife 13 (113) is in contact with the mucous membrane surface, marking is formed. Of course, even when the operating section 4 fully strokes and the needle-like knife 13 (113) sticks out most from the flexible sheath 2, there is no possibility that the needle-like knife 13 (113) comes into contact with the muscle layer. Marking can be made by using another treatment tool, and the above-described cauterization must not be employed if the region to be excised of the mucous membrane can be recognized through the observing portion W.

Figure 17:
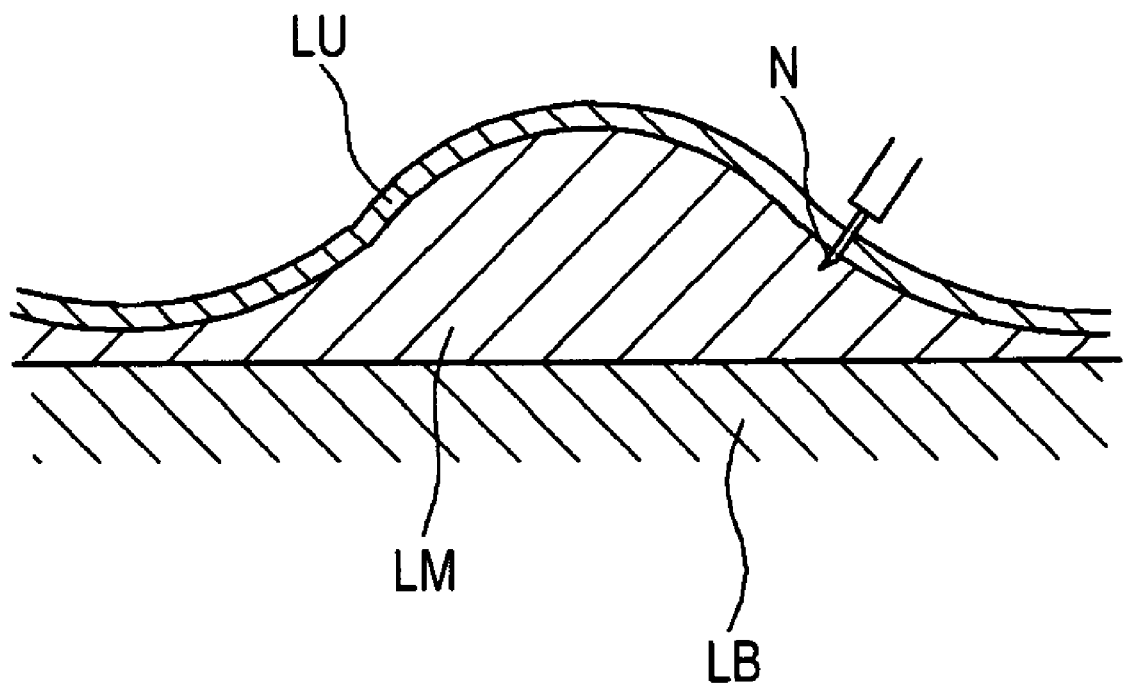
FIG. 17 is a sectional view of the tissue, showing local injection into the diseased mucosal region.

Next, as shown in FIG. 17, normal saline solution is locally injected to the inside of the diseased mucosal region D. For this, the high-frequency treatment tool 1 is temporarily extracted from the treatment tool insertion channel, and instead of this, a local injecting section provided with an injection needle N on the front end of a flexible tube is inserted into the treatment tool insertion channel C. Herein, between the muscle layer LB and the mucosal layer LU, the submucosal layer LM exists, and the injection needle N penetrates the mucosal layer LU and punctures up to the submucosal layer LM, and then injects the normal saline solution. As a result, the submucosal layer LM is evaginated and bulged. Bulging of the submucosal layer LM is for separating the mucosal layer LU from the muscle layer LB for smooth and safe treatment.

After sufficiently bulging the submucosal layer LM, the local injecting section is extracted from the treatment tool insertion channel C and the high-frequency treatment tool 1 is inserted again. Then, the flexible sheath 2 of the high-frequency treatment tool 1 and the annular end wall P formed by the front-end faces 2a and 20a of the hard cylinder 20 are made to contact any of the outer edge of the diseased mucosal region D. Herein, the annular end wall P is made to correctly face the mucosal layer LM and the annular end wall P is slightly pressed against the mucous membrane surface while the pressing force is minimized.

Figure 18A:
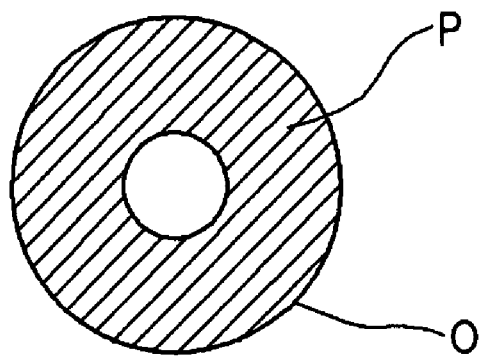
FIGS. 18A to 18C are explanatory views concerning an area occupied by the annular end wall.
Figure 18B:
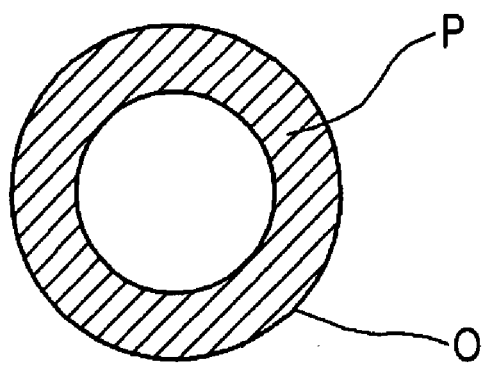
Figure 18C:
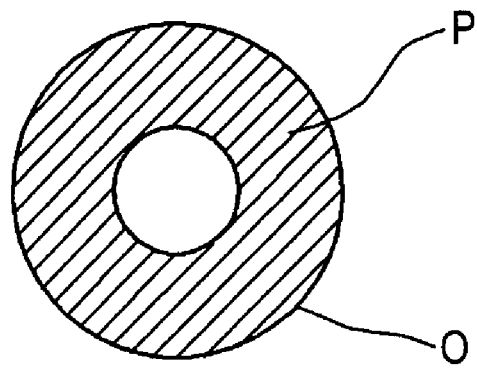

Herein, when the front end of the high-frequency treatment tool 1 is pressed against the mucous membrane surface, to prevent the mucosal layer LM from being deformed by pressure, the area of the annular end wall P must be widened. However, the needle-like knife 13 (113) must have a certain degree of thickness in terms of its strength, and to smoothly insert the needle-like knife 13 (113) into the through hole 21 (121) of the hard cylinder 20 (120), even when the hole diameter of this through hole 21 (121) is minimized, as shown by the shaded area in FIG. 18A, the annular end wall P is widened to 90% at most of the circle O of the front end outer diameter of the high-frequency treatment tool 1. In addition, especially in the first embodiment, communicating channels 24 are formed inside the annular end wall P, and to stably secure the contact area between the stopper wall 22 and the rear end face 20b of the hard cylinder 20 while securing sufficient communicating areas of the communicating channels 24, as shown by the shaded area in FIG. 18B, the area of the annular end wall P must be set to at least 65% or more. In detail, desirably, the area ratio of the annular end wall P is set to approximately 80% (the second embodiment) and approximately 85% (the first embodiment) as shown by the shaded area in FIG. 18C. Thereby, when the high-frequency treatment tool 1 is pressed against the mucosal layer LM, the mucous membrane surface is pressed to its minimum limit, so that a sufficient distance to the muscle layer LB can be secured.

Figure 19:
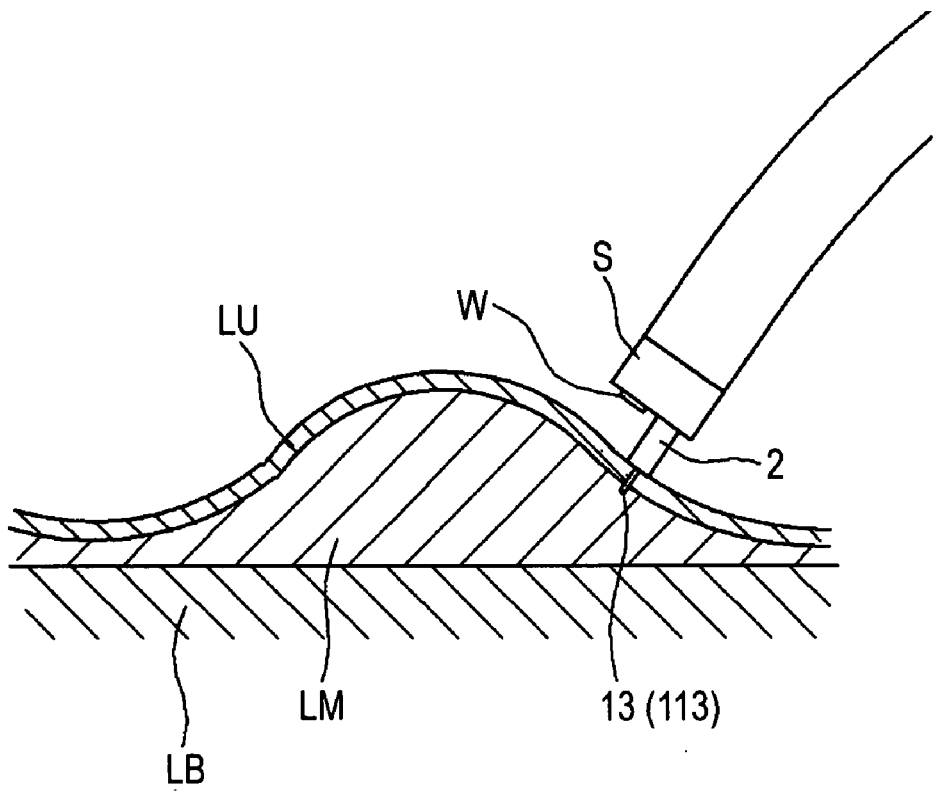
FIG. 19 is a sectional view of the tissue, showing incision with the high-frequency treatment tool.

Then, in the first embodiment, the operating section 4 is operated to stick-out the needle-like knife 13 from the front end of the stopper member 14, and during this, a high-frequency current is supplied to the needle-like knife 13. When the needle-like knife 13 sticks out most, as shown in FIG. 19, the needle-like knife 13 penetrates the mucosal layer LU and is guided to the submucosal layer LM, and then incision of the diseased mucosal region D is started. Then, by moving the endoscope inserting portion S and bending the angle portion thereof under observation through the observing portion W, incision is performed along the cauterizing spots B.

Herein, the needle-like knife 13 sticks out only to the position at which the stopper projections 22 come into contact with rear end face 20b of the hard cylinder 20, so that the maximum sticking-out length from the flexible sheath 2 is set larger than the thickness of the mucosal layer LU and shorter than the total thickness of the mucosal layer LU and the submucosal layer LM. Then, in the second embodiment, the operating section 4 is operated to protrude the high-frequency knife 113 from the through-hole 121 of the hard cylinder 120 provided inside the flexible sheath 2. Here, although the base end face of the hard cylinder 120 is a face orthogonal to the axis line thereof, since the lead-in member 122 is arranged at the base end face of the hard cylinder 120, the front-end portion of the rod-like electrode 14 of the high-frequency knife 113 is reliably lead into the through-hole 121. During this time, a high-frequency current is applied to the high-frequency knife 113. When the high-frequency knife 113 has reached the maximum protruding condition, as shown in FIG. 19, the high-frequency knife 113 penetrates through the mucosal layer LU and is lead to the submucosal layer LM, whereby incision of the diseased mucosal area D is started. In this condition, under observation by the observing portion W, by moving the endoscope inserting portions and by operating an angle portion thereof so as to curve, incision is conducted so as to proceed along the cauterizing spots B. Here, it has been set so that the high-frequency 113 protrudes only up to the position where the stopper surface 15c of the blade portion 15 of the high-frequency knife 113 abuts against the base end face of the hard cylinder 120, the maximum protrusion length from the flexible sheath 2 is greater than the thickness dimension of the mucosal layer LU and is shorter than the total thickness dimension of the mucosal layer LU and submucosal layer LM.

The submucosal layer LM is bulged by local injection, so that the mucosal layer LU can be reliably incised unless the annular end wall P extremely presses and deforms the mucous membrane surface. In addition, the mucosal layer LU is incised with no damage on the muscle layer LB. In the first embodiment, the sticking-out portion of the needle-like knife 13 from the front end of the flexible sheath 2 is centered so as to match with the central axis line of the flexible sheath 2 by the above-described coupling of the tapered surfaces. In the second embodiment, since the four blade portions 15 have been provided in the high-frequency knife 113 and the outer surfaces 15b of the blade portions 15 almost slidingly contact with the inner circumferential wall of the through-hole 121 of the hard cylinder 120, the part of the high-frequency knife 113 protruded from the flexible sheath 2 is stably held, and is stably held in a condition almost coincident with the central axis line of the flexible sheath 2 without movement such as shaking and staggering of the high-frequency knife 113 owing to a reaction force that acts from the mucosal layer LU during incision.

Figure 20:
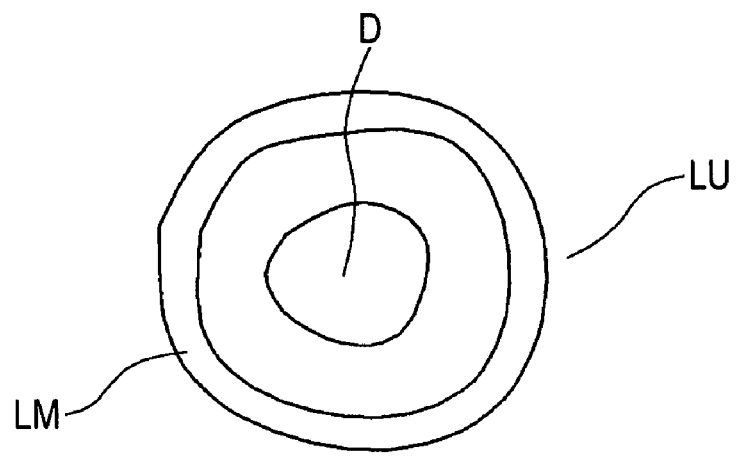
FIG. 20 is a plan view including the diseased mucosal region, showing a state in that the incision with the high-frequency treatment tool is finished.

Therefore, even when the position of the front end of the needle-like knife 13 (113) is not confirmed through the observing portion W of the endoscope inserting portion S, the treatment can be safely performed. As a result, as shown in FIG. 20, on the outer circumference of the diseased mucosal region D, the mucosal layer LU is incised and the submucosal layer LM is exposed. In FIG. 20, the entirety of the diseased mucosal region D is incised at a time, however, if the diseased mucosal region D is wide, it is desirable that a part of this is incised and exfoliated and this operation is repeated.

Figure 21:
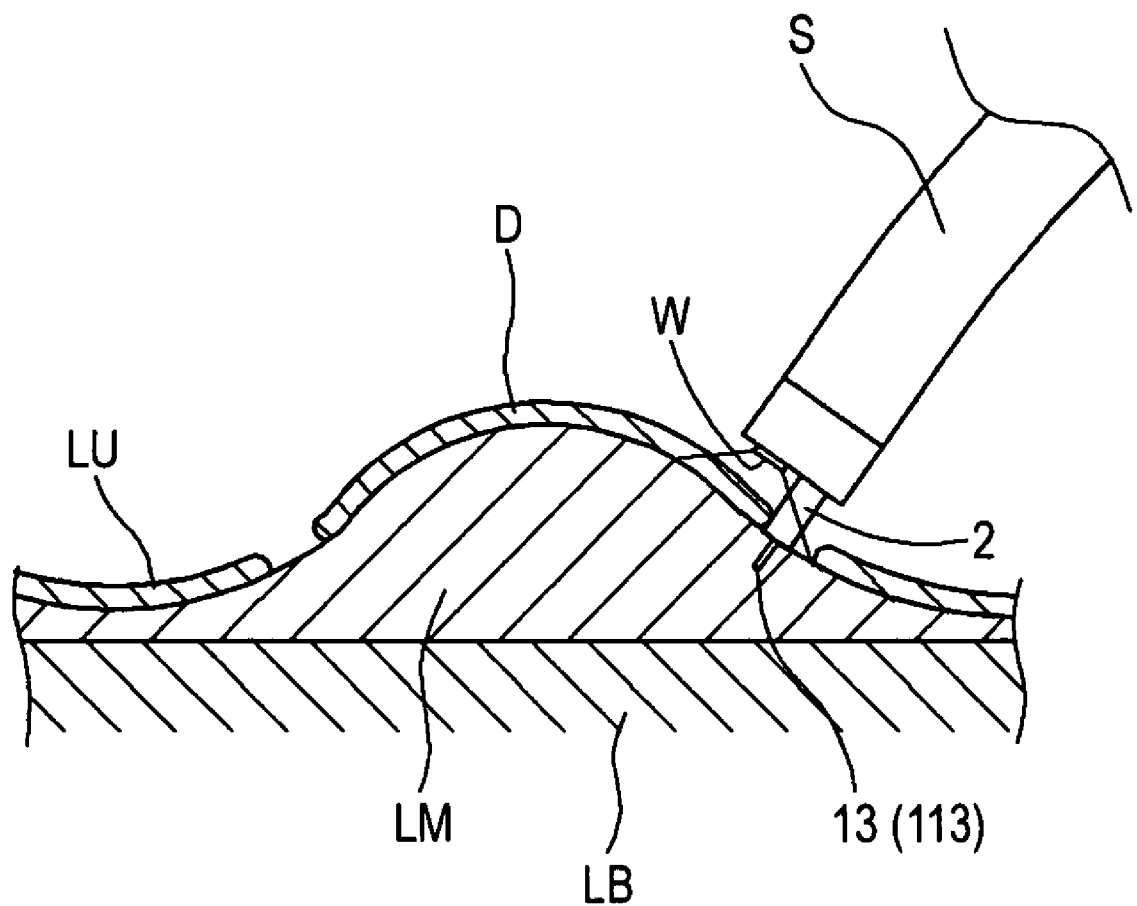
FIG. 21 is a sectional view of the tissue, showing a state during exfoliation of the mucous membrane.

Only by incising the entire circumference of the diseased mucosal region D, the mucosal layer LU cannot be removed. Namely, the mucosal layer LU and the muscle layer LB are linked to each other via the fiber submucosal layer LM, so that it is necessary to cut the fibers and exfoliate the mucosal layer from the muscle layer LB. This exfoliation of the mucous membrane can be performed by using the high-frequency treatment tool 1. Namely, as shown in FIG. 21, the needle-like knife 13 (113) sticking out from the flexible sheath 2 of the high-frequency treatment tool 1 is advanced to the portion of the submucosal layer LM exposed by incision, and this needle-like knife 13 (113) is moved horizontally or swung to cut the submucosal layer LM. This operation can be easily performed by bending the front end portion of the endoscope inserting portion S. As a result, the mucous membrane is quickly and efficiently exfoliated.

During the above-described exfoliation of the mucous membrane and during the above-described incision, the treated portion may bleed. Therefore, normal saline solution is supplied by a high pressure to the inside of the flexible sheath 2 from the connection port 3a of the connecting pipe 3. In the first embodiment, in the front end face of the hard cylinder 20, between the stopper projections 22, communicating channels 24 communicating with the connection port 3a are opened on the inner side of the through hole 21 of the hard cylinder 20. In the second embodiment, at the front end of the hard cylinder 120, between the mutually adjacent blade portions 15 and 15 of the high-frequency knife 113, the communicating channels 123 that lead to the connection port 3a are opened at the inner side of the through hole 121 of the hard cylinder 120. Therefore, by jetting the normal saline solution toward the bleeding portion from the communicating channels 24 (123), the bleeding portion can be washed away quickly. This washing operation can be performed while the treatment to exfoliate the mucous membrane is continued, that is, while the needle-like knife 13 (113) sticks out from the front end of the flexible sheath 2.

When performing the exfoliation of the mucous membrane, normal saline solution must be replenished. The diseased mucosal region D has been already bulged by local injection of the normal saline solution, and the supplied normal saline solution may flow out and is absorbed by the body during the incision and the bulged portion may contract. Therefore, to maintain the bulged state of the submucosal layer LM, the mucous membrane is exfoliated while the normal saline solution is replenished. This replenishment of the normal saline solution can be performed through the communicating channels 24 (123). In this case, the needle-like knife 13 (113) is drawn closer to the base end side than the hard cylinder 20 (120), the annular end wall P is made to contact the submucosal layer LM, and the normal saline solution is injected to the inside of the flexible sheath 2 from the connection port 3a of the connecting pipe 3, whereby the normal saline solution can be more efficiently supplied and directly injected to the submucosal layer LM. As a result, the submucosal layer LM to be exfoliated can be maintained in a bulged state.

Thus, the replenishment of normal saline solution does not require troublesome operations of extracting the high-frequency treatment tool 1 inserted in the treatment tool insertion channel C and inserting a syringe instead, and does not interrupt the exfoliation of the mucous membrane. Therefore, the treatment is made efficient and quick in this point. In addition, no member sticks out from the annular end wall P, so that the front end of the groove 21 (121) can be made to contact the submucosal layer LM, and normal saline solution can be accurately supplied to a necessary portion. Thereby, the exfoliation of the mucous membrane can be safely and quickly performed with the needle-like knife 13 (113) while the submucosal layer LM is reliably maintained in the bulged state.

In addition, it is also possible to make negative pressure suction act on the mucosal layer LU if necessary. Suction can be carried out during execution of a mucosal stripping treatment as well as before or after the treatment. In either case, suction piping is connected to the connection port 3a, and suction control is carried out by a foot switch or the like. Therefore, when suction is necessary, by operating the high-frequency treatment tool 1 so as to produce a negative pressure in the suction piping by operating the foot switch, suction from the body can be carried out via the communicating channels 24 (123).

The entire disclosure of each and every foreign patent application from which the benefit of foreign priority has been claimed in the present application is incorporated herein by reference, as if fully set forth.

What is claimed is:

1. A high-frequency treatment tool comprising:
a flexible sheath that can be inserted into a treatment tool insertion channel of an endoscope;
a treatment tool body that is provided inside the flexible sheath, the treatment tool body comprising a flexible cord and a high-frequency knife to which a high-frequency current is applied, the high-frequency knife being formed at a front-end of the flexible cord; and
a hard cylinder having an electrical insulating property, the hard cylinder being inserted and fixed inside the flexible sheath so that a front-end face of the hard cylinder forms almost the same plane as a front-end face of the flexible sheath,
wherein the high-frequency knife comprises a plurality of blade portions radially provided at predetermined positions in an axial direction of the high-frequency knife, each of the plurality of blade portions including an engaging part, and
wherein, when a part of the high-frequency knife protrudes from the hard cylinder, the engaging parts of the plurality of blade portions abut against a rear end portion of the hard cylinder so that: the high-frequency knife is engaged with the hard cylinder; and adjacent communicating channels are formed between the plurality of blade portions, through which liquid flows.

2. The high-frequency treatment according to claim 1, wherein the hard cylinder has a hole diameter larger than an outer diameter of the high-frequency knife,
the rear-end portion of the hard cylinder is formed into a tapered surface inclined inward from its outer circumferential side to its inner circumferential edge,
front-end faces of the plurality of blade portions are formed into inclined portions serving as the engaging parts, the inclined portions corresponding to the tapered surface of the hard cylinder, and
when the part of the high-frequency knife protrudes from the front-end face of the hard cylinder, the inclined portions of the plurality of blade portions abut against the tapered surface of the hard cylinder so that the high-frequency knife is engaged with the hard cylinder.

3. The high-frequency treatment tool according to claim 2, wherein the hard cylinder comprises ceramic, and the plurality of blade portions comprise metal.

4. The high-frequency treatment tool according to claim 2, wherein an annular end wall is formed by the front-end face of the flexible sheath and the front-end face of the hard cylinder, and
the annular end wall occupies an area of 65 through 90 percent of a circle formed by a front-end outer diameter of the high-frequency treatment tool.

5. The high-frequency treatment tool according to claim 1, wherein the high-frequency knife further comprises a rod-like electrode that can be inserted through the hard cylinder in a loosely fitted manner, said plurality of blade portions being provided on a base-end side of the rod-like electrode,
each of the plurality of blade portions has: an outer surface having a size to almost contact with an inner circumferential surface of the hard cylinder; and a stopper surface, serving as the engaging part, formed at a base-end portion of the blade portion, the stopper surface having a length in a radial direction of the hard cylinder, and
when the part of the high-frequency knife protrudes from the hard cylinder, the stopper surfaces of the plurality of blade portions abut against a rear-end face of the rear-end portion of the hard cylinder so that the high-frequency knife is engaged with the hard cylinder.

6. The high-frequency treatment tool according to claim 5, wherein the hard cylinder comprises a ceramic material, the high-frequency knife is formed of a metal material, and
the plurality of blade portions are provided on the rod-like electrode at three points with intervals of 120° or at four points with intervals of 90°.

7. The high-frequency treatment tool according to claim 5, wherein the front-end face and the rear-end face of the hard cylinder having faces orthogonal to an axis line of the hard cylinder, and
wherein the rear-end portion of the hard cylinder has a tapered surface leading a front-end of the high-frequency knife to a through hole of the hard cylinder.

* * * * *